United States Patent
Inda et al.

(10) Patent No.: US 6,792,396 B2
(45) Date of Patent: Sep. 14, 2004

(54) INTERFACE DEVICE AND METHOD FOR A MONITORING NETWORK

(75) Inventors: Allan G. Inda, Milwaukee, WI (US); Daniel J. Nowicki, Cedarburg, WI (US); Michael J. Horvath, Port Washington, WI (US); Patrick A. Van Ryzin, Pewaukee, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 69 days.

(21) Appl. No.: 10/109,542

(22) Filed: Mar. 28, 2002

(65) Prior Publication Data

US 2003/0187618 A1 Oct. 2, 2003

(51) Int. Cl.$^7$ ................................ G06F 11/00
(52) U.S. Cl. ................ 702/188; 702/19; 702/32; 702/121; 702/188; 340/539.22; 340/870.06; 375/220; 600/301; 455/557
(58) Field of Search .............. 702/19, 21, 32, 702/33, 121, 122, 182, 183, 186, 187, 188, FOR 103, 104, 115, 119, 134, 135, 170, 171; 340/870.06, 870.27, 573.3, 539.22; 455/657; 375/220; 600/305, 301; 128/846

(56) References Cited

U.S. PATENT DOCUMENTS

| 5,465,082 A | * | 11/1995 | Chaco ................... 340/825.54 |
| 5,867,821 A | * | 2/1999 | Ballantyne et al. ............ 705/2 |
| 6,440,071 B1 | | 8/2002 | Slayton et al. |
| 2003/0003127 A1 | * | 1/2003 | Dalal .......................... 607/32 |
| 2003/0120164 A1 | * | 6/2003 | Nielsen et al. .............. 600/513 |

FOREIGN PATENT DOCUMENTS

| WO | WO 92/04806 A1 | 3/1992 |
| WO | WO 00/25284 A2 | 5/2000 |
| WO | WO 00/42911 | 7/2000 |
| WO | WO 01/43631 A1 | 6/2001 |
| WO | WO 02/064032 A2 | 8/2002 |

OTHER PUBLICATIONS

Vargas, Home–Based Monitoring of Cardiac Patents, Jun. 1998, IEEE Article, vol.: 4793, pp. 133–136.*

Sukuvaara et al., "Intelligent Patient Monitor– Its Function and User Interface", Jul. 1992, IEEE Article, vol.:2485, pag s 373–376.*

"Octanet™ Connectivity Device Service Manual"; (81–page product manual); 418264–003, Revision B; GE Marquette Medical Systems, Inc. (Jan. 14, 2000).

"Octacomm Connectivity Device Operator/Service Manual", (155–page product manual); Software Versions 1 and 2; 418264–001, Revision C; GE Marquette Medical Systems, Inc. (Jan. 8, 1999).

Search Report, GB 0306477.1, Jul. 10, 2003.

* cited by examiner

Primary Examiner—Marc S. Hoff
Assistant Examiner—Elias Desta
(74) Attorney, Agent, or Firm—Audrus, Sceales, Starke & Sawall

(57) ABSTRACT

An interface device receives data from a plurality of sensors and transmits the data over a communication network to one or more of a plurality of monitors. The interface device is capable of operating in both a peripheral mode of operation and a stand-alone mode of operation for the plurality of monitors. In another embodiment, a monitor is connected to a plurality of interface devices by way of a communication network. A separate visible physical communication link or other identification link is used to visually identify which of the interface devices is serving as a peripheral device for the monitor.

36 Claims, 8 Drawing Sheets

FIG. 8

INTERFACE DEVICE AND METHOD FOR A MONITORING NETWORK

FIELD OF THE INVENTION

This invention relates to monitoring systems and, in particular, relates to interface devices and methods used in a monitoring network to acquire data from a system under test.

BACKGROUND OF THE INVENTION

Monitoring networks and devices are known for monitoring systems under test. For example, in medical applications, patient monitors are known for monitoring patients. A typical patient monitor includes a display, one or more operator input devices, one or more input ports for connecting the monitor to sensors that acquire data from the patient, and a microprocessor or other signal processor for processing the data acquired from the patient.

A large variety of sensors exist that may be used for data acquisition. For example, in medical applications, it may be desirable to receive data from sensors such as a carbon dioxide ($CO_2$) sensor, a ventilator sensor, a urometer sensor, a pulse oximetry ($SPO_2$) sensor, an ECG sensor, a respiration sensor, an invasive or non-invasive blood pressure sensor, and so on. Within each of these different sensor types, a wide range of specific sensors exist that are available from different manufacturers, and it is desirable to be able to provide health care facilities with the option of connecting patient monitors to a variety of different sensors available from different sensor manufacturers.

Interface devices are sometimes used to increase the number and/or variety of sensors that can be used to acquire data for a monitoring device. Often, one or more such interface devices are connected to a communication network along with one or more monitoring devices. A need exists for an interface device that can operate in a variety of modes of operation. For example, in some situations, it is desirable to have an interface device that operates in a stand-alone mode of operation, e.g., by transmitting data over a communication network to a variety of monitoring devices. This allows the data from the sensors to be made available at any monitoring device that wishes to view the data. In other instances, it is desirable to have an interface device that serves as a peripheral device for a monitoring device. For example, it may be desirable for the interface device to operate from an operator's perspective as if the interface device is directly connected to the monitoring device, or in some other manner which results in the operator perceiving the monitoring device as being more closely associated with the particular interface device than with other interface devices on the communication network.

Additionally, such interface devices and monitoring device are often connected to a communication network along with other interface devices and monitoring devices. When establishing a network connection between a particular patient monitoring device and a particular interface device, a need exists for a way to ensure that the correct two devices are connected together and to make connecting the two devices together as easy for the operator as possible.

A monitoring system and method that meets one or more of these needs would be highly desirable.

BRIEF SUMMARY OF THE INVENTION

According to a first preferred embodiment, an interface device for a monitoring system comprises a communication interface, a microprocessor, and a memory. The communication interface is adapted to connect the interface device to a communication network to transmit data acquired by the interface device using a plurality of sensors over the communication network. The memory is programmed to provide the interface device with a peripheral mode of operation and a stand-alone mode of operation. In the peripheral mode of operation, the interface device operates as a peripheral device for one of a plurality of monitors. In the stand-alone mode of operation, the interface device operates as a stand-alone device for multiple ones of the plurality of monitors. In particular, in the stand-alone mode of operation, the interface device operates as a stand-alone device available to transmit the data from the sensors to multiple ones of the plurality of monitors by way of the communication network.

According to another preferred aspect, a monitoring system comprises a communication network, a sensor, an interface device, and a plurality of monitors. The sensor is capable of acquiring data from a system under test. The interface device is coupled to the sensor to receive the data from the system under test. The interface device and each of the plurality of monitors is coupled to the communication network. The interface device has a peripheral mode of operation and a stand-alone mode of operation. The interface device operates as a peripheral device for a selected one of the plurality of monitors in the peripheral mode of operation, and operates as a stand-alone device available to transmit the data to each of the plurality of monitors in the stand-alone mode of operation.

According to another preferred aspect, a monitoring system comprises a communication network, a plurality of sensors, a monitor, a plurality of interface devices, and an identification link. The plurality of sensors are capable of acquiring data from a plurality of systems under test. The monitor has a display and is coupled to the communication network. The plurality of interface devices are coupled to respective ones of the plurality of sensors to receive the data from the systems under test. The plurality of interface devices are also coupled to the communication network. A selected one of the plurality of interface devices operates as a peripheral device for the monitor. The identification link provides a separate physical connection between the monitor and the selected one of the plurality of interface devices to thereby provide a visual indication which one of the plurality of interface devices is operating as the peripheral device for the monitor.

BRIEF DESCRIPTION OF THE DRAWINGS

FIG. 8 is a screen display of a monitor in the system of FIG. 1 in which the monitor displays its own data alongside data from another monitor, and with the data from the other monitor being merged with data from an interface device.

DETAILED DESCRIPTION OF PREFERRED EMBODIMENTS

Figure 1:
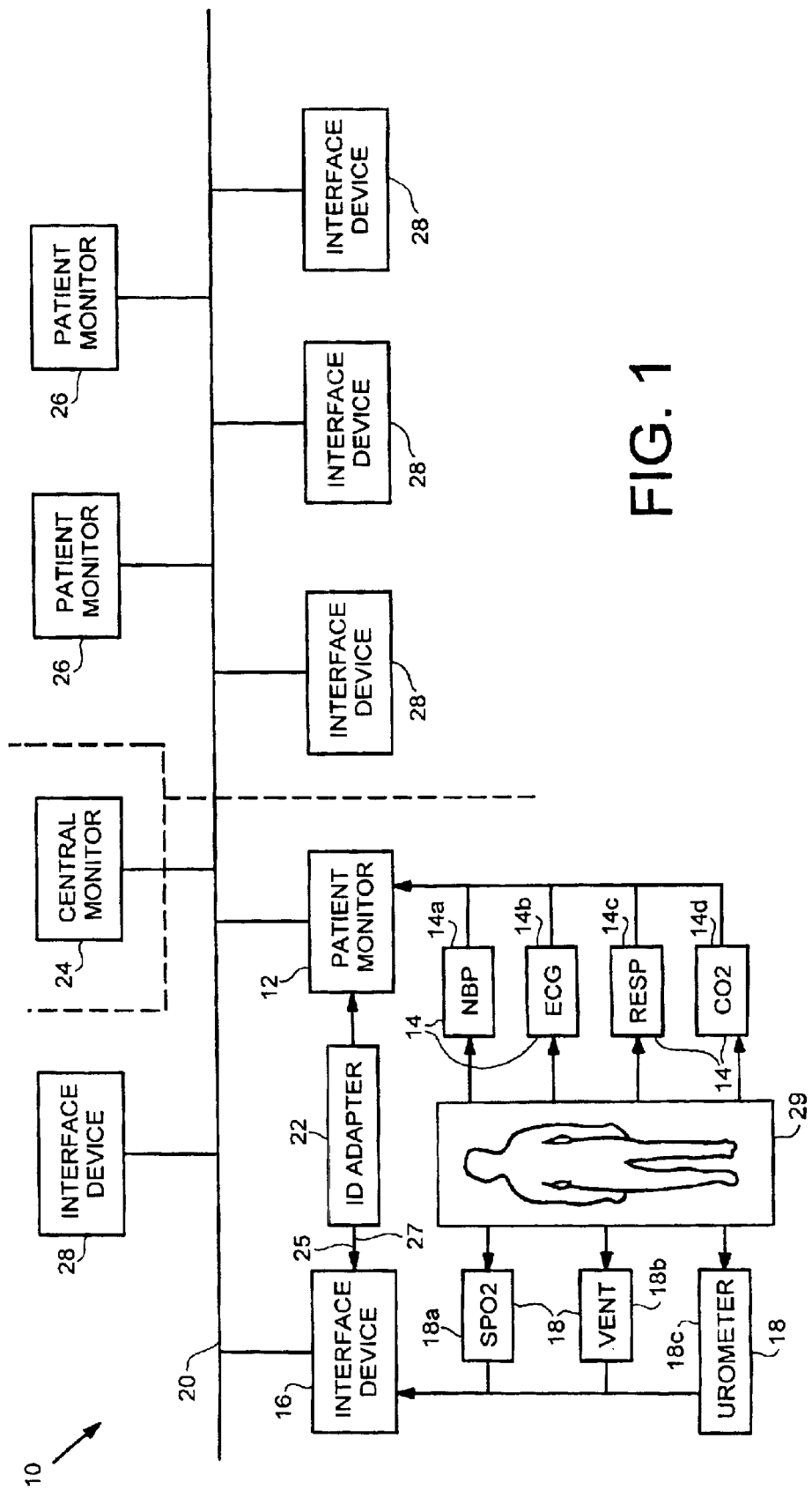
FIG. 1 is a block diagram of a patient monitoring system according to a preferred embodiment.
Figure 2:
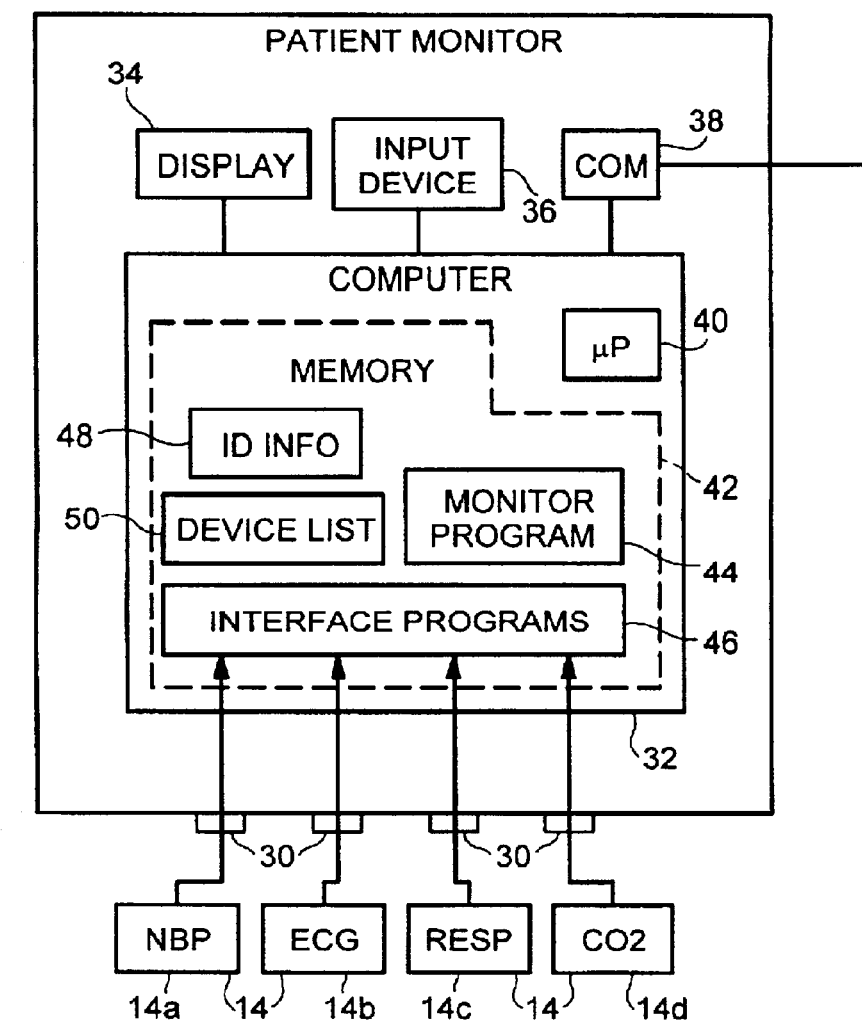
FIG. 2 is a block diagram showing a patient monitor of the system of FIG. 1 in greater detail.
Figure 3:
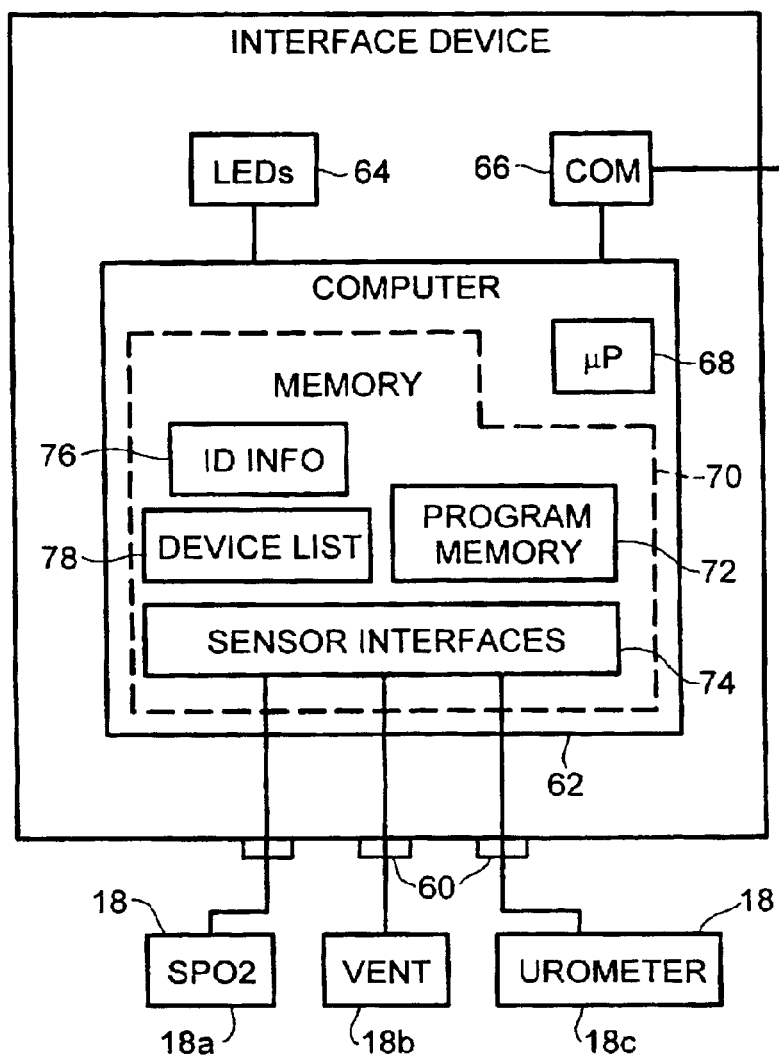
FIG. 3 is a block diagram showing an interface device of the system of FIG. 1 in greater detail.

Referring now initially to FIGS. 1–3, an overview of a monitoring system 10 according to a preferred embodiment is shown. The monitoring system 10 comprises a monitor 12, a first plurality of sensors 14, an interface device 16, a second plurality of sensors 18, a communication network 20, an identification adapter 22, a central monitor 24, a plurality of additional monitors 26, and a plurality of additional interface devices 28.

As shown in FIG. 2, which shows the monitor 12 in greater detail, the monitor 12 includes a plurality of input ports 30, a computer 32, a display 34, an input device 36 and a communication interface 38. The computer further includes a microprocessor 40 and a memory 42. The memory 42 is programmed and stores such things as one or more monitor programs 44, one or more interface programs 46, identification information 48, and a device list 50.

The monitor 12 is connected to the first plurality of sensors 14. These connections may be made by analog or digital (parallel or serial) communication links, by direct hardwired or wireless connection of the sensor to the monitor 12, or by another arrangement. In the preferred embodiment, the sensors 14 are connected to the monitor 12 by way of input ports 30. In one embodiment, the input ports 30 are each uniquely configured for a particular type of sensor, such that a given input port 30 may only be used with a particular type of sensor. Alternatively, the input ports may be identical ports, such as RS-232 ports, to provide a standard communication interface for connecting sensors from various manufacturers to the monitor 12. A combination of these two approaches may also be used.

The sensors 14 may include a variety of different types of sensors that acquire different types of data. In the preferred embodiment, the monitor 12 is a portable patient monitor and is used to continuously monitor parameters from a patient 29. In this embodiment, the sensors 14 are used by the monitor 12 to acquire physiological data from the patient 29 and may include, for example, a ventilator sensor, a urometer sensor, a pulse oximetry (SPO2) sensor, a carbon dioxide (CO2) sensor, an electrocardiograph (ECG) sensor, a respiration sensor, an invasive blood pressure sensor, a non-invasive blood pressure (NBP) sensor, cardiac output sensor, impedance cardiography sensor, electroencephalograph (EEG) sensor and so on. In FIG. 1, the sensors 14 are shown as including an NBP sensor 14a, and ECG sensor 14b, a respiration sensor 14c and a CO2 sensor 14d. The monitor 12 is programmed to support each of the different types of sensors 14 to which it is connected. To this end, the monitor 12 includes the interface programs 46 which are useable to interpret and process the data acquired the different sensors which are supported by the monitor 12.

The display 34 and the input device 36 of the monitor 12 provide an operator interface by which operator inputs are acquired and data acquired by the sensors 14 and 18 is displayed to the operator. The communication interface 38 connects the monitor 12 to the communication network 20, allowing the monitor 12 to transmit information to and receive information from other devices on the communication network 20. The monitor program 44 is one or more programs executed by the microprocessor 40 to control operation of the monitor 12. The identification information 48 includes an identifier by which the monitor 12 is identified for communication on the communication network 20. The device list 50 is a list of devices (monitors, interface devices) active on the communication network 20.

The interface device 16 is connected to the second plurality of sensors 18. With reference to FIG. 3, which shows the interface device 16 in greater detail, the interface device 16 includes a plurality of input ports 60, a computer 62, a plurality of indicators 64 such as LEDs, and a communication interface 66. The input ports 60 are connected to the sensors 18 and receive the data acquired by the sensors from the patient 29. The communication interface 66 connects the interface device to the communication network 20 to transmit the data from the sensors 18 over the communication network 20. The computer further includes a microprocessor 68 and a memory 70. The memory 70 includes memory that stores programs executed by the microprocessor 68 for operation of the interface device, such as program memory 72 and sensor interface memory 74, as well as memory that stores other information such as identification information 76 and a device list 78.

The sensors 18 may be completely different or may overlap with the sensors 14. Again, these connections may be made by analog or digital (parallel or serial) communication links, by direct connection of the sensor to the interface device 16, or by another arrangement. The sensors 18 are preferably connected to the interface device 16 by way of identical input ports 60 (e.g., RS-232 ports) disposed on the interface device 16, which provide a standard communication interface for connecting sensors from various manufacturers to the interface device 16. The sensors 18 may include a variety of different types of sensors that acquire different types of data as described above in conjunction with the sensors 14. In the patient monitoring embodiment, the sensors 18 are used by the interface device 16 to acquire physiological data from the patient 29. In FIG. 1, the sensors 18 are shown as including an SPO2 sensor 18a, a ventilator sensor 18b, and a urometer sensor 18c.

The interface device 16 is programmed to support each of the different types of sensors 18 to which it is connected. To this end, the interface device includes the interface programs 74 which are useable to interpret and process the data acquired by the sensors 18. The sensors 18 each include memory (not shown) that stores identification information (e.g., device type) for the sensor 18. When one of the sensors 18 is initially connected to the interface device 16, this information is transmitted to the interface device 16 so that the interface device 16 can determine the type of sensor to which it is connected. Based on this information, the interface device 16 uses a particular interface program 74 to interpret and process the data from the particular sensor 18. In this regard, it may be noted that the interface device 16 may be used to serve as a universal interface device for a variety of different types of sensors. In other words, when a decision is made to support a new type of sensor, interface software for the new type of sensor is developed and programmed into the interface device 16. Any type of monitor or other device that is connected to the communication network 20 then has access to the data acquired by the new type of sensor by way of the interface device 16. There is no need to develop interface software for each of these different types of monitors individually.

It may be noted that in some cases sensors may be connected to a monitor or interface device only indirectly and a certain amount of preprocessing may occur before data from a particular sensor is transmitted to the monitor or the interface device. For example, in connection with the ventilator sensor 18b, this sensor is likely to be provided as part of or attached to a ventilator system having its own computer system and an output port. The output port of the ventilator system may be connected to an input port 60 of the interface device 16, and data may be transferred to the interface device 16 via the connection made between these two ports. The interface device 16 is therefore connected to the sensor 18b by way of the ventilator computer system, and the data from the ventilator sensor 18b is made available to the interface device 16 by the ventilator computer system, as opposed to by the sensor 18b itself directly. Similar arrangements may be used for other devices such as respirators. In other cases, particular sensors may be directly connected to the monitors and interface devices.

The communication network 20 connects the patient monitor 12, the interface device 16, the central monitor 24, the patient monitors 26 and the interface devices 28. The communication network 20 may be a hardwired or wireless network and may be a local area network, metropolitan area network, or wide area network such as the Internet. In the embodiment of FIG. 1, the communication network is a hospital monitoring network or other patient monitoring network. The patient monitors 12, 26 and interface devices 16, 28 may be located throughout different rooms of the healthcare facility. The monitors 26 may be the same or similar in construction and operation to the monitor 12, and the interface devices 28 may be the same or similar in construction and operation to the interface device 16. The patient monitors 26 and the interface devices 28 are connected to additional sensors that acquire physiological data from other patients. For simplicity, the additional sensors and additional patients are not shown in FIG. 1. Other types of monitors or interface devices may also be used. For example, one of the monitors 26 may be a clinical information system, which is in essence a device that monitors and stores data transmitted on the communication network 20. Other non-monitoring, non-data acquiring devices may also be connected to the network 20, although these devices are not shown in FIG. 1.

The identification adapter 22 is disposed between the monitor 12 and the interface device 16. Preferably, the identification adapter 22 is embedded in an electrical cable 27 which forms a dedicated communication link 25 between the monitor 12 and the interface device 16. The dedicated communication link 25 is separate from the communication network 20 and provides a direct connection between the monitor 12 and the interface device 16. In the preferred embodiment, the cable 27 connects to the monitor 12 by way of an open one of the input ports 30 used to connect the monitor 12 to the sensors 14, and connects to the interface device 16 by way of an open one of the input ports 60 used to connect the interface device 16 to the sensors 18. The cable 27 is preferably bi-directional, so that either end may be coupled to either the monitor 12 or the interface device 16.

In one embodiment, data acquired by the interface device 16 using the sensors 18 is transmitted to the monitor 12 by way of the communication network 20 and not the dedicated communication link 25. Alternatively, if the communication link 25 has sufficient bandwidth, data may be transmitted by way of the communication link 25. In this embodiment, the purpose of the cable 27 is limited to providing a reliable way of determining which two devices (i.e., which interface device and which patient monitor) are connected together. Because the operator can see a physical, hardwired connection between the monitor 12 and the interface device 16, there is little opportunity for confusion on the operator's part as to which two devices are connected together. This avoids a situation in which the operator is under a mistaken impression that the monitor 12 is configured to receive data for one patient from one interface device, when in fact the monitor 12 is actually configured to receive data for a different patient from a different interface device. Of course, it would also be possible to transmit the data acquired by the sensors 18 by way of the dedicated communication link 25 instead of by way of the communication network 20.

The identification adapter 22 includes memory (not shown) that stores device type information that is transmitted to the interface device 16 and that is used by the interface device 16 to distinguish the identification adapter 22 from some other type of device, such as a sensor. This is akin to the device type information stored and transmitted by the sensors 18. This allows the interface device 16 to recognize that it is connected to an identification adapter (and thus, by way of the identification adapter, to a patient monitor) as opposed to some other type of device, such as a sensor.

Figure 4:
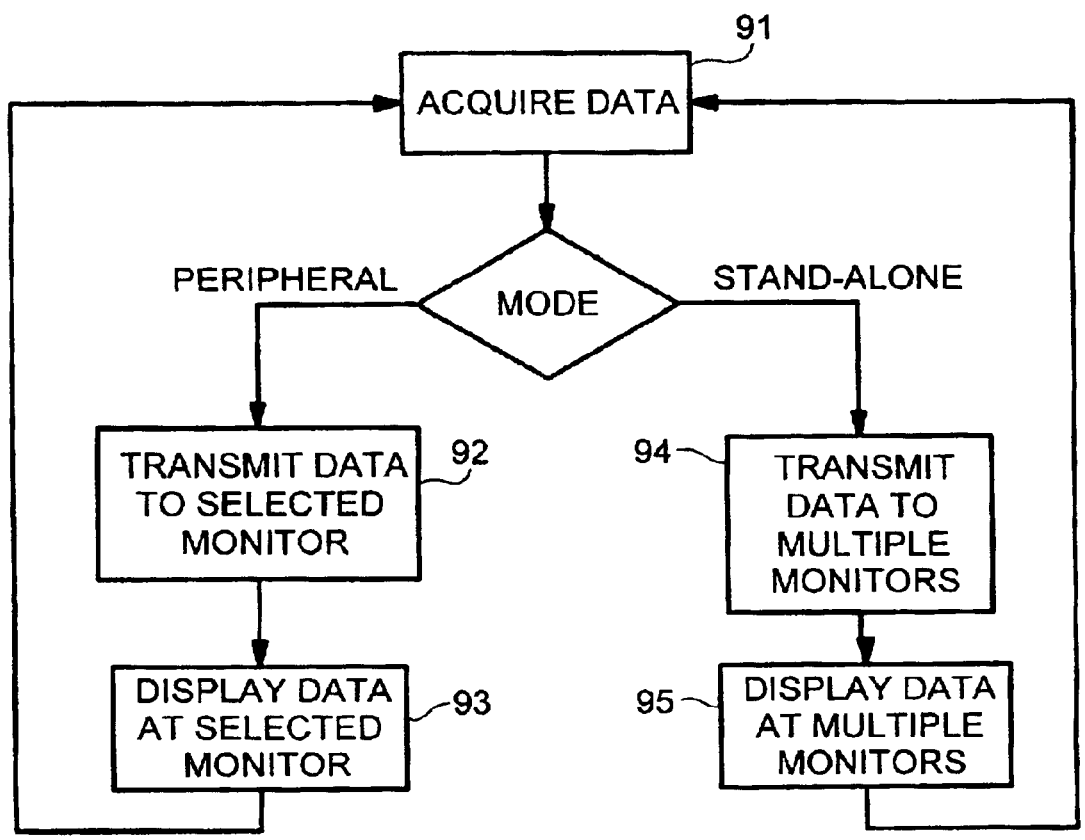
FIG. 4 is a flowchart showing the operation of the system of FIG. 1 in either a stand-alone mode of operation or a peripheral mode of operation.

Referring now also to FIG. 4, an overview of the operation of the system 10 is illustrated. The interface device 16 has two modes of operation, namely, a peripheral mode of operation and a stand-alone mode of operation.

In the peripheral mode of operation, the interface device 16 operates as a peripheral device for one of the monitors 12, 26. By way of example, it is assumed herein that the interface device 16 is configured to operate as a peripheral for the monitor 12, although the interface device 16 could just as easily be configured at other times to operate as a peripheral for one of the other patient monitors 26. In FIG. 4, at step 91, data is acquired from the patient 29 using the sensors 18 connected to the interface device 16. Assuming the interface device 16 is operating as a peripheral device for the monitor 12, then the data is transmitted from the interface device 16 to the monitor 12 at step 92. At step 93, the data is displayed by the monitor 12.

In one embodiment, in the peripheral mode of operation, the data acquired by the interface device 16 is available to remaining ones of the plurality of monitors 26 only through the monitor 12. Thus, the system 10 may be configured such that data acquired by any of the monitors 12 and 26 may be displayed at any of the other monitors 12 and 26. This allows data acquired from one patient to be viewed by a physician without the physician necessarily having to be at the patient's bedside. In the peripheral mode of operation, the data acquired by the interface device 16 is available to the monitors 26 along with the data from the monitor 12. However, the monitors 26 are not permitted to directly access the data acquired by the interface device 16; rather, access to the data acquired by the interface device 16 is granted through the monitor 12. Thus, when the interface device 16 is in the peripheral mode of operation, access to the data acquired by the interface device 16 is obtained in a manner which is substantially the same as the manner in which access is obtained to the data acquired by the monitor 12. Data acquired by the interface device 16 using the sensors 18 is merged with data acquired by the monitor 12 using the sensors 14. From an operator interface perspective, data from the interface device 16 is viewed at one of the monitors 26 by viewing the data acquired by the monitor 12, and little or no differentiation exists between data acquired by the interface device 16 and data acquired by the monitor 12. Of course, other configurations are also possible.

Additionally, the monitors 26 each maintain a list 50 of interface devices 28 on the communication network 20. The monitors 26 can then be configured to display this list to an operator (in response to the reception of appropriate operator inputs), such that an operator may select one of the interface devices 28. For example, an operator at one of the operator monitors 26 may wish to select a particular one of the interface devices 28, adjust alarm thresholds for a particular one of the parameters monitored by the selected interface device 28, and then monitor the selected parameter to thereby be alerted when the parameter exceeds the alarm threshold. In the preferred embodiment, when the interface device 16 is in the peripheral mode of operation, and when an operator of one of the monitors 26 displays a list of the interface devices on the communication network 20, the interface device 16 is not included among the list of interface devices displayed to the operator.

It may also be noted that, in the peripheral mode of operation, some of the data transmitted to the monitor 12 by the interface device 16 may not be displayed by the monitor 12 but may instead be passed through the monitor 12 to one of the monitors 26, such as a clinical information system. For example, intravenous (IV) pump data may be passed through the monitor 12 to a clinical information system for charting. Other parameters unknown to the monitor 12 may be passed through as well. For example, if a particular sensor 18 is not supported by the monitor 12 but is supported by the interface device 16, the data from the particular sensor 18 may simply be passed through the monitor 12 to the other monitors 26 on the rest of the communication network 20.

In the stand-alone mode of operation, the interface device 16 operates as a stand-alone device for the monitors 12, 26. The interface device 16 is available to transmit data directly to any or all of the monitors 12, 26 by way of the communication network 20, depending on which monitors 12, 26 are configured to receive such data. As previously noted, in one embodiment, each of the monitors 12, 26 maintains a list of interface devices 16, 28 which are present on the communication network 20 and which are available to operate in the peripheral mode of operation. When the interface device 16 is in the stand-alone mode of operation, the interface device 16 appears on this list for each of the monitors 12, 26. In response to suitable operator inputs, any subset of the monitors 12, 26 may be configured to display data from the interface device 16 and to silence alarms, adjust alarm threshold values, initiate graph generating functions, change patient demographic and identification information, and others. It may be noted that although the interface device is available to transmit data to multiple ones of the monitors 12 in the stand-alone mode of operation, 26, the subset of monitors which are configured to receive the data may some times actually consist of zero monitors.

Referring again to FIG. 4, FIG. 4 shows operation of the interface device 16 in the case where multiple monitors 12, 26 are configured to receive the data from the interface device 16. Thus, in FIG. 4, in the stand-alone mode of operation, the data from the interface device 16 is transmitted to multiple ones of the monitors 12, 26 at step 94. At step 95, the data is displayed by the multiple ones of the monitors 12, 26.

Figure 5:
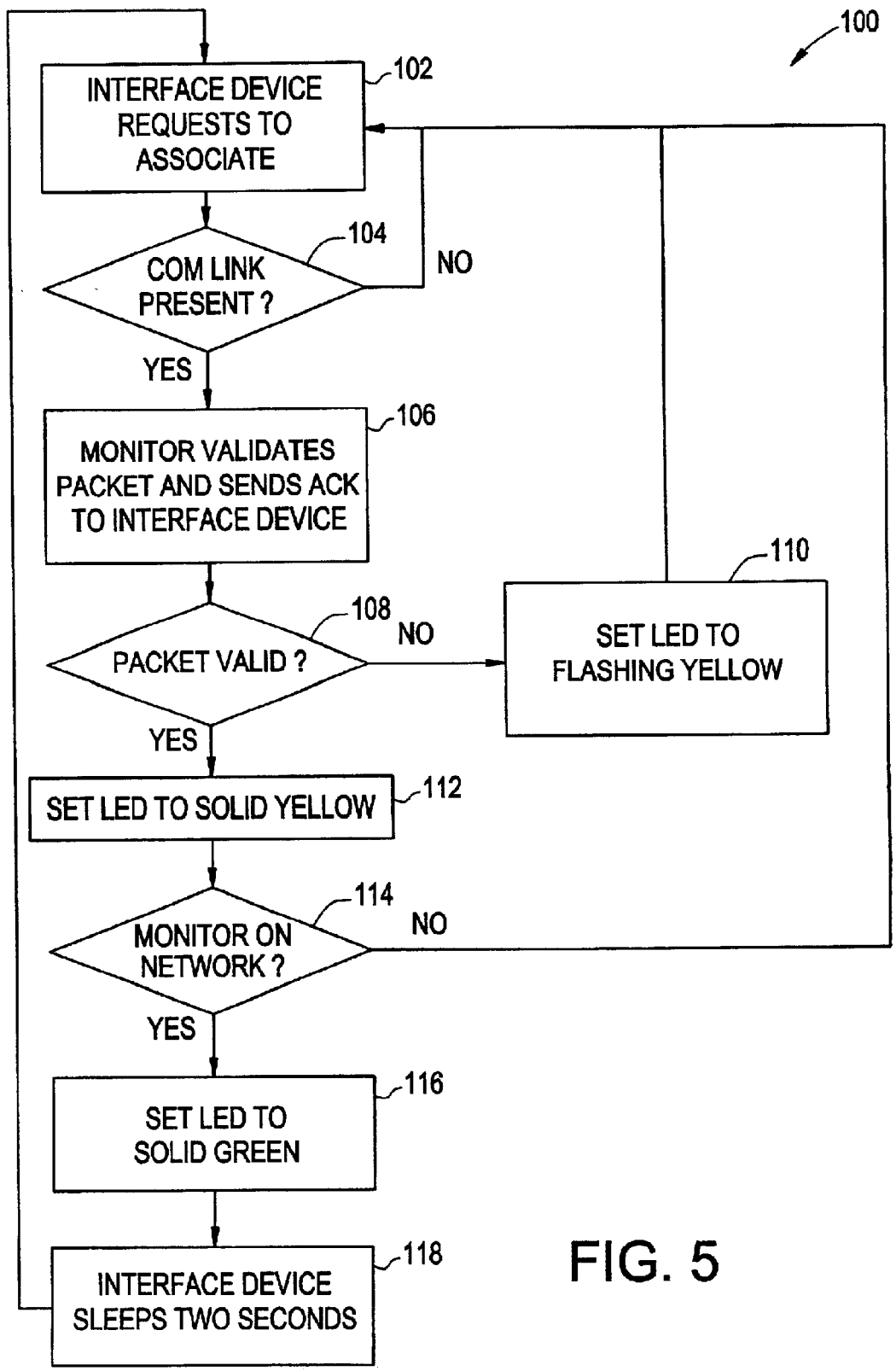
FIG. 5 is another flowchart showing operation of an interface device to associate with a monitor in the system of FIG. 1.

Referring now to FIG. 5, an embodiment of an association process 100 in which the interface device 16 enters a peripheral mode of operation is illustrated. By default, the interface device 16 is in the stand-alone mode of operation unless action is taken by an operator to which causes the system 10 to configure the interface device 16 in the peripheral mode of operation. Upon detecting that the interface adapter 22 has been connected to one of the input ports 60 of the interface device 16, the interface device 16 and the monitor 12 initiate an auto-association process in which the interface device 16 and the monitor 12 establish communication with each other and the interface device 16 becomes a peripheral of the monitor 12. From the standpoint of a human operator, the operator connects the interface device 16 and the monitor 12 with the cable 27, and this initiates an auto-detect sequence wherein the interface device 16 and the monitor 12 detect the presence of the cable 27 and the interface device 16 enters the peripheral mode of operation.

More specifically, by way of example, at step 102, the interface device 16 requests to associate with a monitor 12 or 26. Preferably, step 102 is implemented by the interface device 16 which attempts to transmit identification information (or a "packet") on the dedicated communication link 25 at periodic intervals. This transmission provides an indication to any listening device (particularly, the monitor 12) that the interface device 16 is available to enter the peripheral mode of operation. The identification information may include the unit name, bed number and IP address of the interface device 16. Sending the unit name and bed number is advantageous if the monitor 12 is a portable monitor which is susceptible to being moved from location to location within a facility. The monitor 12 may then further prompt the operator to confirm the unit name of the interface device 16, to provide further assurance that the correct two devices are connected together.

The monitor 12 may also change its own unit name and bed number to be similar to that of the unit name and bed number of the interface device 16. This is advantageous in that the unit name and bed number of the monitor 12 can be automatically configured to match that of a location within the facility by way of the data sent from the interface device 16 via the dedicated communication link 25. In this example, the unit name and bed number of the interface device 16 pre-configured such that it matches the physical location of the interface device 16 with the facility, such as a room number and bed location.

At step 104, if the dedicated communication link 25 is not present, then the process 100 returns to step 102. On the other hand, if the dedicated communication link 25 is present at step 104, then the identification information is successfully transmitted by way of the dedicated communication link 25 to the monitor 12. The process 100 then proceeds to step 106.

At step 106, monitor 12 validates the identification information and sends an acknowledgment to the interface device 16 by way of the communication link 25. The acknowledgment transmitted by the monitor 12 includes identification information (e.g., IP address) for the monitor 12. At step 108, the interface device 16 performs a checksum operation to confirm that the identification information from the monitor 12 is valid. If the checksum operation is not successful, this indicates a faulty connection between the interface device 16 and the monitor 12. Accordingly, at step 110, operator feedback is provided indicating the faulty connection on the dedicated communication link 25 (e.g., a flashing yellow LED 64 on the interface device 16), and the process 100 returns to step 102.

Conversely, at step 112, if the checksum operation is successful, then operator feedback is provided indicating an "association pending" condition (e.g., a solid yellow LED 64 on the interface device 16), and the process 100 proceeds to step 114. At step 114, the interface device 16 attempts to establish a connection with the monitor 12 on the communication network 20. If no connection can be established, then the process returns to step 102.

If connection is established at step 114 then, at step 116, operator feedback is provided indicating successful association (communication on both the network 20 and the link 25). The operator feedback may take the form, for example, of a solid green LED 64 on the interface device 16.

After step 116, the mode of operation of the interface device 16 is thereby changed from the stand-alone mode of operation to a peripheral mode of operation. The process then proceeds to step 118, waits for a predetermined amount of time (e.g., two seconds), and then returns to step 102. By virtue of regularly returning to step 102, the interface device 16 regularly confirms that it is still connected to the monitor 12. During this time, the interface device 16 may transmit real time waveform data and/or numeric parameter data to the monitor 12.

In the preferred embodiment, the cable 27 is provided which forms a communication link 25 between the interface device 16 and the monitor 12. The cable 27 provides a physical connection between the interface device 16 and the monitor 12 which is visible to the operator, and therefore serves to visually identify which two devices are connected together. Other types of physical connections may be used to implement a visual identification link. For example, a device as simple as a string with mechanical or electronic keys at both ends may be used. If electronic keys are used, for example, the electronic keys may take the form of connectors which each pin selectively tied high or low. Each connector then represents a stored N-bit number (with N corresponding to the number of pins) which is read by the monitor 12 at one end and the interface device 16 at the other end. The monitor 12 and interface device 16 then locate each other on the communication network 20 by locating the device with the matching key. Other arrangements are also possible. It may also be noted that the use of a visual identification link may be employed not only with interface devices that are capable of both a peripheral and stand-alone mode of operation, but also with interface devices that are only capable of a peripheral mode of operation.

In alternative embodiments, no visible communication link is used (e.g., no identification adapter 22, no communication link 25, and so on), and the interface device 16 enters the peripheral mode of operation entirely in response to requests transmitted by way of the communication network 20. For example, an operator input may be received at the monitor 12 which indicates that the operator wishes to have the interface device 16 configured to operate as peripheral for the monitor 12. Each interface device 16, 28 broadcasts its presence on the communication network 20 and each monitor 12, 26 maintains a list of interface devices available on the communication network 20. When the operator wishes to select an interface device to be configured as a peripheral, a list of available interface devices is displayed to the operator at the monitor 12. Operator inputs are then received which indicate the operator's selection of a particular interface device 16, 28 to serve as a peripheral. The interface device 16 changes from the stand-alone mode of operation to the peripheral mode of operation in response to receiving a request from the monitor 12 to enter the peripheral mode of operation. To provide safe assurance that the correct two devices are associated, a device name may be made visible on the housing of the interface device 16, which the operator may then read and compare to the number of the interface device presented on the display of the monitor 12.

Figure 6:
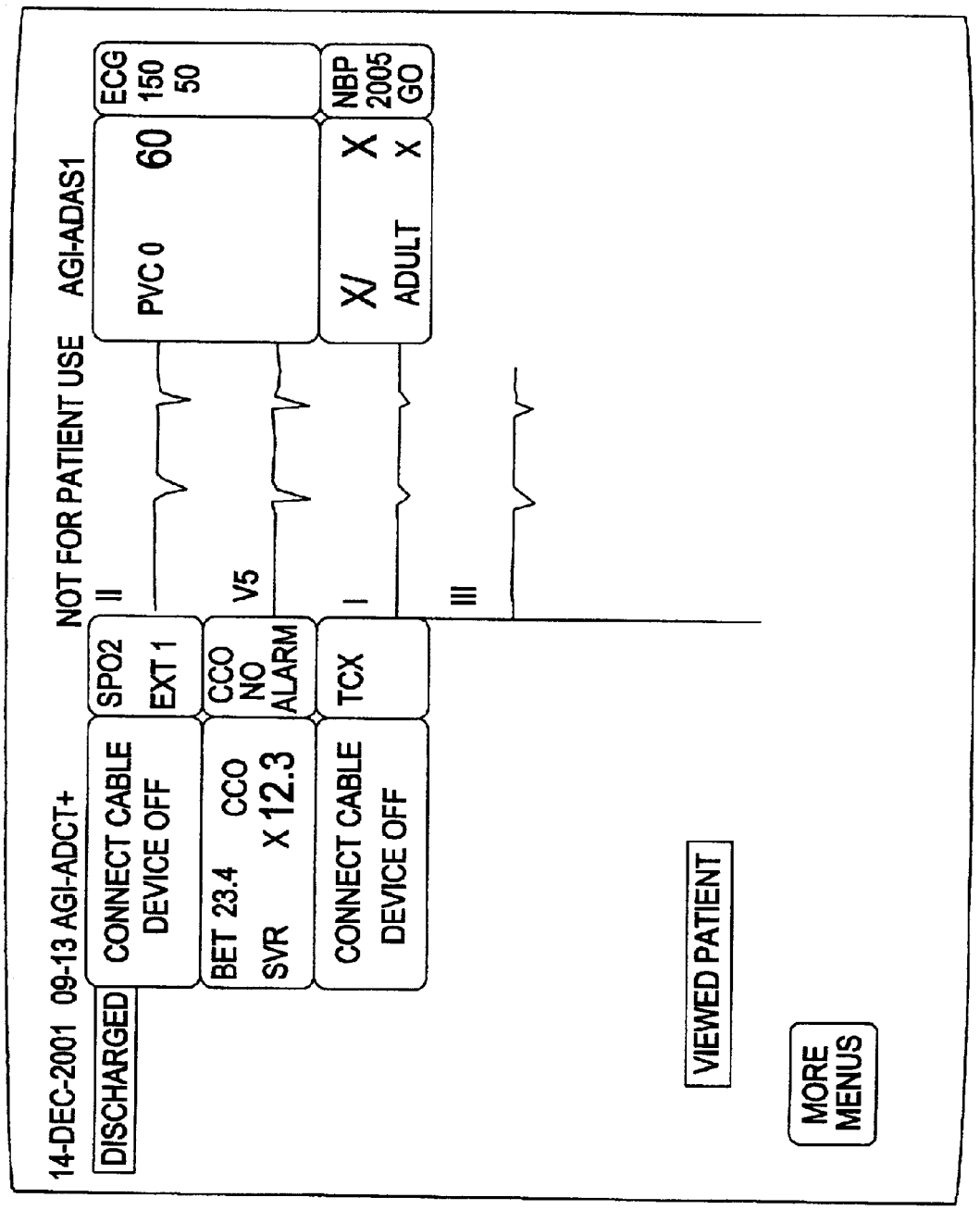
FIG. 6 is a screen display of a monitor in the system of FIG. 1 in which the monitor displays data from an interface device alongside the monitor's own data.
Figure 7:
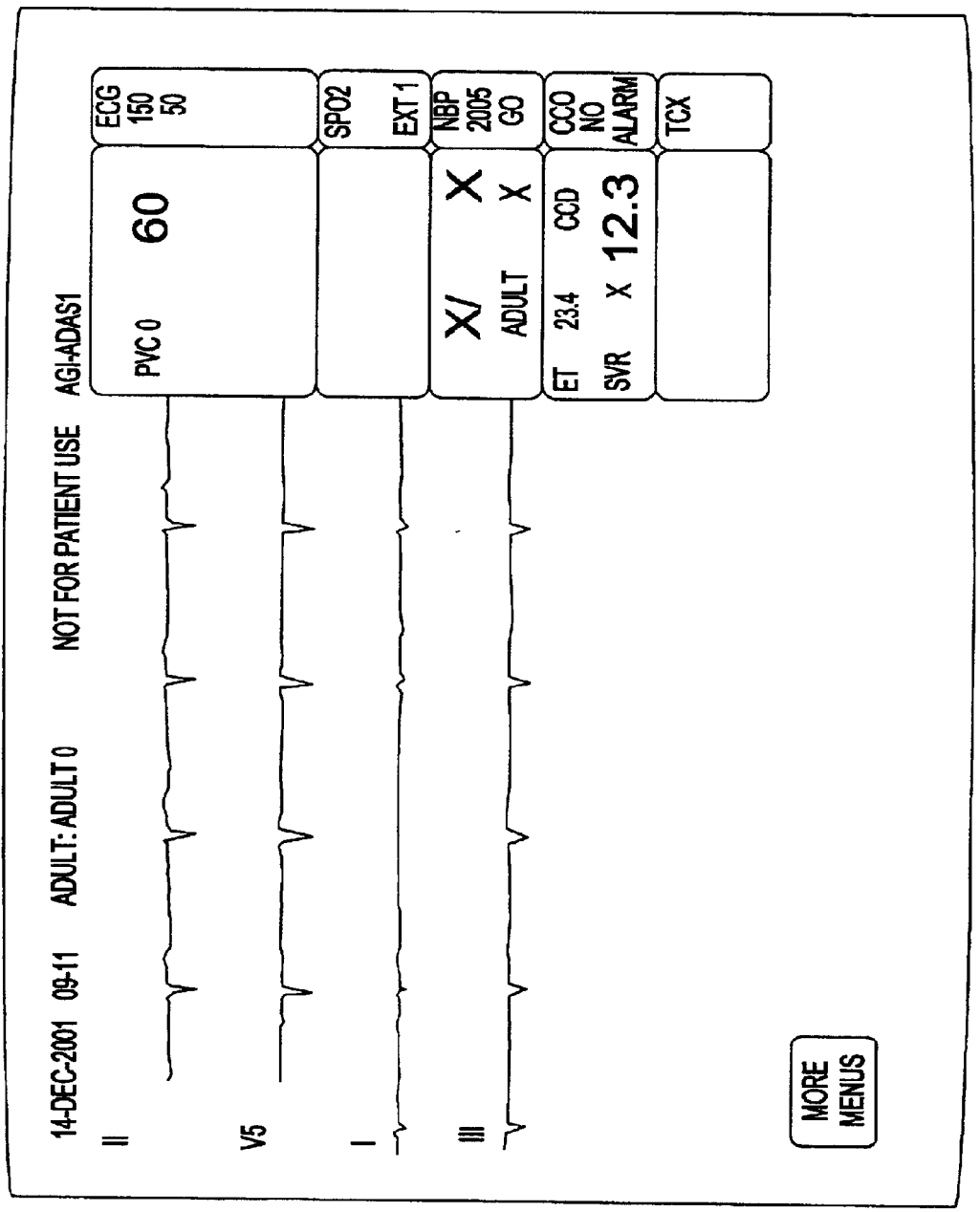
FIG. 7 is a screen display of a monitor in the system of FIG. 1 in which the monitor displays data from an interface device merged along with its own data.
Figure 8:
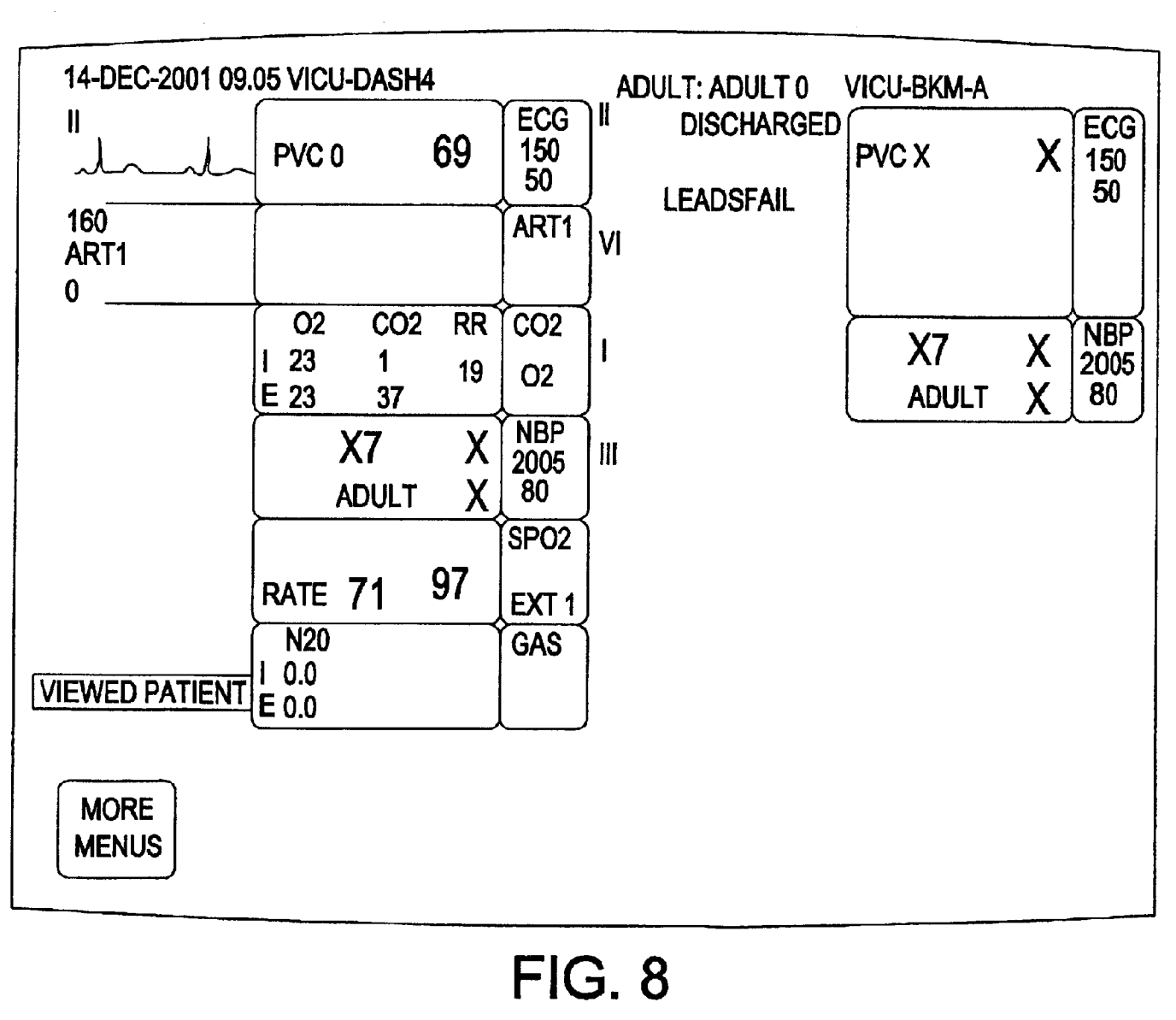

Referring now to FIGS. 6–8, a plurality of exemplary screen displays are shown. In FIG. 6, the interface device 16 is in the stand-alone mode of operation. The data is displayed at the monitor 12 in a split view mode, such that the right-hand side of the screen shows the data acquired using the sensors 14 and the left-hand side of the screen shows data acquired using the sensors 18. The left and right are potentially two different patients, but they could be the same patient.

In FIG. 7, the interface device 16 is in a peripheral mode of operation. The data from the interface device 16 in FIG. 6 is displayed by the monitor 12, except that the monitor 12 has merged this data in with its own local data. It appears that data from the interface device 16 is local to the monitor 12.

In FIG. 8, one of the patient monitors 26 is displaying data in a split view mode. The right side of the display is locally acquired data for the monitor 26. The left side of the display is a remote view of the data acquired by the monitor 12. The data from the monitor 12 contains a combination of data that is locally acquired by the monitor 12 and data acquired by the interface device 16.

Many changes and modifications may also be made to the invention without departing from the spirit thereof. The scope of these changes will become apparent from the appended claims.

What is claimed is:

1. An interface device for a monitoring system, comprising:
   a communication interface, the communication interface being adapted to connect the interface device to a communication network to transmit data acquired by the interface device using a plurality of sensors over the communication network; and
   a microprocessor and a programmed memory coupled to the microprocessor, the memory being programmed to provide the interface device with a peripheral mode of operation and a stand-alone mode of operation;
   wherein, in the peripheral mode of operation, the interface device operates as a peripheral device for a first one of a plurality of monitors, the first monitor configured to receive and process data from sensors that are coupled to the first monitor and a system under test, and configured to execute a monitor program related to data acquired by the interface device from the plurality sensors;
   wherein, in the stand-alone mode of operation, the interface device operates as a stand-alone device available to transmit the data from the sensors to multiple ones of the plurality of monitors by way of the communication network.

2. An interface device according to claim 1,
   wherein, in the peripheral mode of operation, (i) the interface device transmits the data acquired by the sensor to the one of the plurality of monitors, (ii) the data is accessible by remaining ones of the plurality of monitors only through the one of the plurality of monitors; and
   wherein, in the stand-alone mode of operation, (i) the data is accessible by remaining ones of the plurality of monitors only through the one of the plurality of monitors, and (ii) the data is displayed by the respective displays of the more than one of the plurality of monitors.

3. An interface device according to claim 1, wherein the data transmitted by the interface device is physiological data pertaining to a physiological condition of a human patient.

4. A monitoring system comprising:
   a communication network;

a sensor, the sensor being capable of acquiring data from a system under test;

an interface device, the interface device being coupled to the sensor to receive the data from the system under test, and the interface device being coupled to the communication network; and a plurality of monitors, each of the plurality of monitors being coupled to the communication network; and wherein the interface device has a peripheral mode of operation and a stand-alone mode of operation, the interface device operating as a peripheral device for a selected first one of the plurality of monitors in the peripheral mode of operation, and the interface device operating as a stand-alone device available to transmit the data to each of the plurality of monitors in the stand-alone mode of operation; and wherein, the first monitor is configured to receive and process data from sensors that are coupled to the first monitor and a system under test, and configured to execute a monitor program related to data acquired by the interface device from the plurality sensors.

5. A system according to claim 4, wherein, in the peripheral mode of operation, (i) the interface device transmits the data acquired by the sensor to the selected one of the plurality of monitors, (ii) the data is displayed by the selected one of the plurality of monitors, and (iii) the data is accessible by remaining ones of the plurality of monitors only through the selected one of the plurality of monitors; and wherein, in the stand-alone mode of operation, the interface device is available to transmit the data individually to each of the plurality of monitors, and the plurality of monitors are each configurable to receive the data acquired by the sensor directly from the interface device by way of the communication network.

6. A monitoring system comprising:

a communication network;

a sensor, the sensor being capable of acquiring data from a system under test;

an interface device, the interface device being coupled to the sensor to receive the data from the system under test, and the interface device being coupled to the communication network; and a plurality of monitors, each of the plurality of monitors being coupled to the communication network; and an identification link, the identification link providing a separate physical connection between the interface device and the selected one of the plurality of monitors to thereby provide a visual indication that the interface device is operating as operating as the peripheral device for the selected one of the plurality of monitors wherein the interface device has a peripheral mode of operation and a stand-alone mode of operation, the interface device operating as a peripheral device for a selected one of the plurality of monitors in the peripheral mode of operation, and the interface device operating as a stand-alone device available to transmit the data to each of the plurality of monitors in the stand-alone mode of operation.

7. A monitoring system comprising:

a communication network;

a sensor, the sensor being capable of acquiring data from a system under test;

an interface device, the interface device being coupled to the sensor to receive the data from the system under test, and the interface device being coupled to the communication network; and a plurality of monitors, each of the plurality of monitors being coupled to the communication network;

wherein the interface device has a peripheral mode of operation and a stand-alone mode of operation, the interface device operating as a peripheral device for a selected one of the plurality of monitors in the peripheral mode of operation, and the interface device operating as a stand-alone device available to transmit the data to each of the plurality of monitors in the stand-alone mode of operation; and wherein the identification link comprises a dedicated communication link, wherein the system further comprises a plurality of additional interface devices, and wherein the interface device and the selected one of the plurality of monitors communicate by way of the dedicated communication link to verify an identity of the interface device operating as the peripheral device for the selected one of the, plurality of monitors.

8. A system according to claim 4, wherein the interface device switches from the stand-alone mode of operation to the peripheral mode of operation in response to receiving a request from the selected one of the plurality of monitors to enter the peripheral mode of operation.

9. A system according to claim 4, wherein the interface device switches from the stand-alone mode of operation to the peripheral mode of operation in response to an operator input received at the selected one of the plurality of monitors.

10. A system according to claim 4, wherein the monitoring system is a patient monitoring system, wherein the system under test is a human patient, and wherein the data acquired from the human patient is physiological data.

11. A system according to claim 10, wherein the sensor is one of an electrocardiograph sensor, a pulse oximetry sensor, a blood pressure sensor, and a carbon dioxide sensor, cardiac output sensor, impedance cardiography sensor, electroencephalograph sensor.

12. A system according to claim 10, wherein the patient monitoring system is located in a healthcare facility.

13. A system according to claim 10, wherein the interface device stores information identifying at least one of a unit name and a bed number with which the interface device is associated, and wherein the interface device transmits the at least one of the unit name and bed number to the selected one of the plurality of monitors.

14. A system according to claim 4, wherein the sensor is one of a first plurality of sensors capable of acquiring data from the system under test, wherein the system further comprises a second plurality of sensors, the second plurality of sensors being capable of acquiring data from the system under test;

wherein the interface device includes a first plurality of input ports, the first plurality of input ports being coupled to respective ones of the first plurality of sensors to receive data at the interface device from the first plurality of sensors; and wherein the selected one of the plurality of monitors includes a second plurality of input ports, the second plurality of input ports being coupled to respective ones of the second plurality of sensors to receive data at the selected one of the plurality of monitors from the second plurality of sensors.

15. A monitoring system comprising:

a communication network;

a sensor, the sensor being capable of acquiring data from a system under test;

an interface device, the interface device being coupled to the sensor to receive the data from the system under test, and the interface device being coupled to the communication network;

a plurality of monitors, each of the plurality of monitors being coupled to the communication network; and wherein the sensor is one of a first plurality of sensors capable of acquiring data from the system under test, wherein the system further comprises a second plurality of sensors, the second plurality of sensors being capable of acquiring data from the system under test;

wherein the interface device includes a first plurality of input ports, the first plurality of input ports being coupled to respective ones of the first plurality of sensors to receive data at the interface device from the first plurality of sensors;

wherein the selected one of the plurality of monitors includes a second plurality of input ports, the second plurality of input ports being coupled to respective ones of the second plurality of sensors to receive data at the selected one of the plurality of monitors from the second plurality of sensors; and wherein, in the peripheral mode of operation, the data acquired by the first plurality of sensors is displayed at the selected one of the plurality of monitors in a manner that is substantially indistinguishable from a manner in which the data acquired by the second plurality of sensors is displayed; and wherein, in the stand-alone mode of operation, the data acquired by the first plurality of sensors is displayed at the selected one of the plurality of monitors in a manner that is readily distinguishable from a manner in which the data acquired by the second plurality of sensors is displayed.

16. An interface device for a patient monitoring system, comprising:

a plurality of input ports, the plurality of input ports being capable of being connected to a respective plurality of sensors to receive data acquired by the sensors from a patient;

a communication interface, the communication interface being adapted to connect the interface device to a communication network to transmit the data from the plurality of sensors over the communication network;

a microprocessor and a programmed memory coupled to the microprocessor, the memory being programmed to provide the interface device with first and second modes of operation, wherein, in the first mode of operation of the interface device, the interface device operates as a peripheral device for a selected first one of a plurality of monitors, such that the interface device transmits the data from the patient to the first monitor, the first monitor configured to receive and process data from sensors that are coupled to the first monitor and a system under test, and configured to execute a monitor program related to data acquired by the interface device from the plurality sensors; and wherein, in the second mode of operation of the interface device, the interface device is available to transmit the data from the sensors to multiple ones of the plurality of monitors by way of the communication network for utilization by the multiple ones of the plurality of monitors, the utilization by the multiple ones of the plurality of monitors comprising, for each monitor, at least one of (a) displaying the data from the sensors and (b) storing the data from the sensors in an electronic patient chart.

17. A patient monitoring system for a healthcare facility, the patient monitoring system comprising:

a communication network;

a first plurality of sensors, the first plurality of sensors being capable of acquiring a first set of data from a human patient, the first set of data pertaining to physiological measurements from the human patient;

a second plurality of sensors, the second plurality of sensors being capable of acquiring a second set of data from the human patient, the second set of data pertaining to additional physiological measurements from the human patient;

a plurality of monitors, the plurality of monitors each being coupled to the communication network and each including a respective display, the plurality of monitors including a first monitor, the first monitor having a first plurality of input ports, the first monitor being coupled to the first plurality of sensors by way of the first plurality of input ports;

an interface device, the interface device being coupled to the communication network, the interface device having a second plurality of input ports, the interface device being coupled to the second plurality of sensors by way of the second plurality of input ports;

wherein, in a first mode of operation, the interface device operates as a peripheral device for the first monitor, such that (i) the interface device transmits the second set of data to the first monitor, (ii) at least some of the second set of data is displayed by the first monitor, and (iii) the second set of data is accessible by remaining ones of the plurality of monitors only through the first monitor; and wherein, in a second mode of operation, the interface device operates as a stand-alone device, such that (i) the interface device transmits the second set of data by way of the communication network to more than one of the plurality of monitors, and (ii) at least some of the second set of data is displayed by the more than one of the plurality of monitors.

18. A method of operation for a patient monitoring network, comprising:

(A) acquiring data from a patient using sensors connected to an interface device;

(B) operating the monitoring network with the interface device in a stand-alone mode operation, including
  (1) transmitting the data from the interface device to a plurality of monitors, and
  (2) displaying the data at the plurality of monitors;

(C) changing the mode of operation of the interface device from the stand-alone mode of operation to a peripheral mode of operation; and (D) operating the monitoring network with the interface device in the peripheral mode operation, including
  (1) transmitting the data from the interface device to a selected first one of the plurality of monitors, the first monitor configured to receive and process data from sensors that are coupled to the first monitor and a system under test, and configured to execute a monitor program related to data acquired by the interface device from the plurality sensors, and (2) displaying the data at the selected one of the plurality of monitors, wherein, in the peripheral mode of operation, the data acquired by the interface device is available to remaining ones of the plurality of monitors only through the selected one of the plurality of monitors.

19. A method according to claim 18, further comprising repetitively broadcasting a message from the interface device indicating that the interface device is available to enter the peripheral mode of operation.

20. A method according to claim 18, wherein the changing step further comprises
   (1) transmitting a request from the selected one of the plurality monitors to the interface device to enter a peripheral mode of operation, and
   (2) receiving and responding to the request at the interface device.

21. A method according to claim 18, wherein the interface device is one of a plurality of interface devices, and wherein the method further comprises maintaining a list of the plurality of interface device that are available to operate in the peripheral mode of operation, the list being maintained in memory devices of at least some of the plurality of monitors.

22. A method of operation for a patient monitoring network, comprising:
   (A) acquiring data from a patient using sensors connected to an interface device, the interface device being one of a plurality of interface devices;
   (B) operating the monitoring network with the interface device in a stand-alone mode operation, including
      (1) transmitting the data from the interface device to a plurality of monitors, and
      (2) displaying the data at the plurality of monitors;
   (C) changing the mode of operation of the interface device from the stand-alone mode of operation to a peripheral mode of operation;
   (D) operating the monitoring network with the interface device in the peripheral mode operation, including
      (1) transmitting the data from the interface device to a selected first one of the plurality of monitors, and
      (2) displaying the data at the selected one of the plurality of monitors,
   (E) maintaining a list of the plurality of interface device that are available to operate in the peripheral mode of operation, the list being maintained in memory devices of at least some of the plurality of monitors; and
   (F) displaying the list to a human operator, and receiving an operator selection indicating which of the plurality of interface devices is available to serve in the peripheral mode of operation;

wherein, in the peripheral mode of operation, the data acquired by the interface device is available to remaining ones of the plurality of monitors only through the selected one of the plurality of monitors.

23. A method of operation for a patient monitoring network, comprising:
   (A) acquiring data from a patient using sensors connected to an interface device;
   (B) operating the monitoring network with the interface device in a stand-alone mode operation, including
      (1) transmitting the data from the interface device to a plurality of monitors, and
      (2) displaying the data at the plurality of monitors;
   (C) changing the mode of operation of the interface device from the stand-alone mode of operation to a peripheral mode of operation;
   (D) operating the monitoring network with the interface device in the peripheral mode operation, including
      (1) transmitting the data from the interface device to a selected first one of the plurality of monitors, the interface device and the selected one of the plurality of monitors being connected by a dedicated communication link, and
      (2) displaying the data at the selected one of the plurality of monitors, and
   (E) exchanging identification information between the interface device and the selected one of the plurality of monitors over the dedicated communication link;

wherein, in the peripheral mode of operation, the data acquired by the interface device is available to remaining ones of the plurality of monitors only through the selected one of the plurality of monitors.

24. A monitoring system comprising:

first means for acquiring a first set of data from a system under test;

second means for acquiring a second set of data from the system under test;

means for displaying the first set of data and the second set of data; and means for receiving the first set of data and transmitting the first set of data on a communication network, wherein, in a first mode of operation, the means for receiving transmits the first set of data exclusively to the means for displaying and, in a second mode of operation, the means for receiving broadcasts the first set of data on the communication network for reception by a plurality of devices capable of displaying the first set of data.

25. A monitoring system comprising:

a communication network;

a plurality of sensors, the plurality of sensors being capable of acquiring data from a plurality of systems under test;

a monitor, the monitor having a display, and the monitor being coupled to the communication network;

a plurality of interface devices, the plurality of interface devices being coupled to respective ones of the plurality of sensors to receive the data from the systems under test, the plurality of interface devices being coupled to the communication network, and a selected one of the plurality of interface devices operating as a peripheral device for the monitor; and an identification link, the identification link providing a separate physical connection between the monitor and the selected one of the plurality of interface devices to thereby provide a visual indication which one of the plurality of interface devices is operating as the peripheral device for the monitor.

26. A system according to claim 25, wherein the identification link comprises a communication link.

27. A system according to claim 26, wherein the interface device and the monitor communicate by way of the dedicated communication link to verify an identity of the selected one of the interface devices.

28. A system according to claim 26, wherein the interface device and the monitor each have an IP address on the communication network, and wherein the interface device and the monitor exchange IP address information by way of the dedicated communication link.

29. A system according to claim 25, wherein the interface device has a peripheral mode of operation and a stand-alone mode of operation, the interface device operating as a peripheral device for the monitor in the peripheral mode of operation, and the interface device operating as a stand-alone device available to transmit the data to the monitor and a plurality of additional monitors in the stand-alone mode of operation.

30. A system according to claim 25, wherein the monitoring system is a patient monitoring system, wherein the system under test is a human patient, and wherein the data acquired from the human patient is physiological data.

31. A system according to claim 25, wherein one of the plurality of sensors is one of an electrocardiograph sensor, a pulse oximetry sensor, a blood pressure sensor, and a carbon dioxide sensor, cardiac output sensor, impedance cardiography sensor, electroencephalograph sensor.

32. A system according to claim 25, wherein the patient monitoring system is located in a healthcare facility.

33. A system according to claim 25, wherein the selected one of the plurality of interface devices stores information identifying at least one of a unit name and a bed number with which the selected one of the plurality of interface devices is associated, and wherein selected one of the plurality of interface devices transmits the at least one of the unit name and bed number to the monitor.

34. A monitoring system, comprising:
   a monitor; and
   an interface device coupled to the monitor and configured to operate in a first operating mode and a second operating mode;
   wherein the monitor handles data acquired by the interface device as if it had been acquired by the monitor if the interface device is in the first operating mode, and handles data acquired by the interface device as if it had been acquired by an independent device if the interface device is in the second operating mode.

35. A monitoring system, comprising;
   a network;
   a monitor coupled to the network; and
   an interface device coupled to the network and configured to operate in a first operating mode and a second operating mode;
   wherein the system handles data acquired by the interface device as if it had been acquired by the monitor if the interface device is in the first operating mode, and handles data acquired by the interface device as if it had been acquired independently of the monitor if the interface device is in the second operating mode.

36. A monitoring system, comprising;
   a network;
   a monitor coupled to the network; and
   an interface device coupled to the network and configured to operate in a first operating mode and a second operating mode;
   wherein the system handles the interface device as if it were a portion of the monitor if the interface device is in the first operating mode, and handles data acquired by the interface device as if it is an independent device if the interface device is in the second operating mode.

* * * * *